April 27, 1943. A. KREBS Plant Pat. 578
ROSE
Filed June 2, 1941
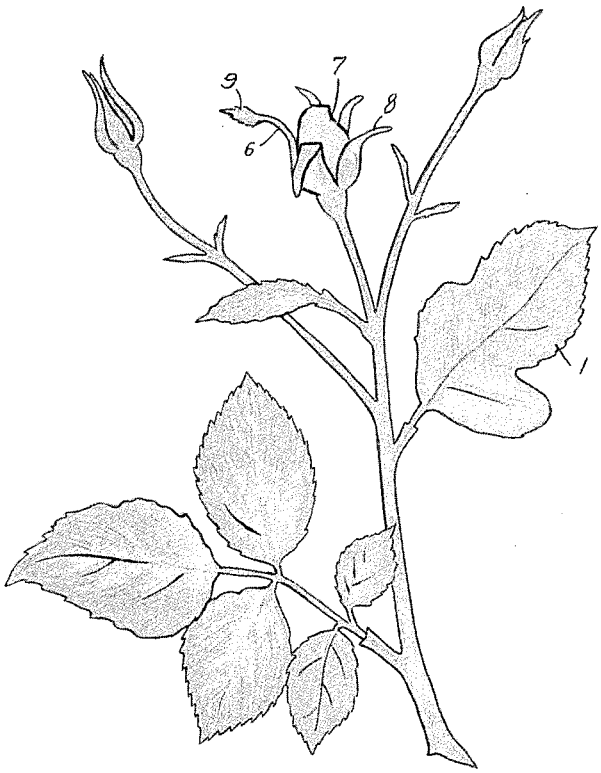
INVENTOR
Alfred Krebs
Lyon & Lyon
ATTORNEYS Patented Apr. 27, 1943

Plant Pat. 578

UNITED STATES PATENT OFFICE

578

ROSE

Alfred Krebs, Montebello, Calif., assignor to Edward E. Marsh, Pasadena, Calif., and himself, jointly Application June 2, 1941, Serial No. 396,317

1 Claim. (Cl. 47—61)

This invention relates to a new and distinctive variety of rose which may be generally designated as a small red rose having some of the characteristics of the common Cecil Brunner. The parentage of the rose bush forming the subject matter of this application is not exactly known. The rose, the subject of this application was produced through cross-pollenization of a rose with a common variety of Cecil Brunner rose. The rose which was used for cross-pollenization with the Cecil Brunner rose was one which had resulted from cross-pollenization theretofore performed and the exact ancestry of this rose is not known and it is an unnamed rose but in several respects, in fact in most respects, is similar to that known as the "World's Fair."

The particular rose illustrated is the first generation cross-pollenization grown from the seed resulting from such cross-pollenization. It is the generation of the rose preceding the rose illustrated in my co-pending application filed June 2, 1941, Serial No. 396,316, and therein referred to as a red rose of the Cecil Brunner type.

As the rose and its foliage are illustrated in the accompanying color print, the print marked Figure 1 shows the first day of opening of the bud with its accompanying foliage.

The new and distinct variety of rose embodying this invention is characterized by the following distinct characteristics:

1. *Color.*—The rose petals are generally red and are of a velvety texture. The edges of the petals shade into a less dense red.

2. Each bud branch of the rose, practically without exception, carries a double leaf formation which may be of the character illustrated at 1 in Figure 1. This double leaf is of substantially the same color characteristics as the other leaves, but is substantially in all respects a double leaf formation in that it is provided with a central rib and veins or veinlets.

3. Each bud structure is provided with at least one long lapel or sepal 6 as illustrated in Figure 1 which extends beyond the bud 7 and is longer than the remaining sepals 8. This sepal has barbed edges as illustrated at 9 in Figure 1 and is similar in texture and shape to a small leaf.

4. The rose bud and developed rose are of a size larger than the ordinary or common variety of Cecil Brunner rose, but are smaller than the red rose commonly known as the "Paul Scarlet." The leaf structure is very similar, except as hereinabove noted both in color and in texture, to the leaf structure of a Cecil Brunner bush rose, except as to the double leaf formation hereinabove set forth.

5. The rose is further characterized by the fact that it has long-lasting characteristics requiring approximately three days for the bud to break, as illustrated in Figure 1, and requiring approximately five days to develop from the bud of Figure 1 to the rose in full bloom.

6. The rose of the bush is characterized further in that it develops its full scent when in full bloom and its scent as the bud opens is very delicate and the scent increases in intensity to where its full scent or fragrance is found in the full bloom.

7. It is further characterized in being a very vigorous grower having this characteristic even to a greater extent than the common variety of Cecil Brunner.

8. The rose is further characterized in that the buds even though closed when cut, will open in water without showing loss in color density and even though the bud be completely closed when placed in water.

9. The rose and the bush are further characterized in being extremely mildew and pest-resistant.

Specifically illustrating the color formation of the bud, open rose and leaf structure as the same are compared with the color plates of The Dictionary of Color by Maerz & Paul, first edition, published by McGraw-Hill Book Company, Inc., 1930, the color of the bud as illustrated in Figure 1 is similar, but darker than the color of, Plate 51, L–5. The leaves are very similar in color throughout their development to that of a common bush variety of Cecil Brunner, the color of the leaves being similar to that designated by Plate 21, L–8. The color of the rose petals may remain substantially constant throughout its development through the successive days with the exception that the edges of the leaves shades to a color which compares with Plate 53, L–8.

The color of the rose is difficult to exactly compare with any color plate because of the leaf texture of the rose. The texture is one having a very velvety appearance, having the distinct sheen of velvet.

I claim:

The rose variety herein described characterized by its velvety carmine buds of velvety texture and sheen wherein each bud has one long sepal characterized further in that the bush has no thorns, the flower has long-lasting qualities, and in that the full scent of the rose flower develops in full bloom and further characterized in that the size of the bud is larger than that of the common variety of bush of the Cecil Brunner rose but is smaller in size than the Paul Scarlet bud.

ALFRED KREBS.